United States Patent [19]

Lott

[11] Patent Number: 5,337,581
[45] Date of Patent: * Aug. 16, 1994

[54] REFRIGERATED WASTE CONTAINER WITH GERMICIDAL LAMP

[76] Inventor: Gene Lott, 896 Chestnut Lake Dr., Marietta, Ga. 30068

[ * ] Notice: The portion of the term of this patent subsequent to Sep. 17, 2008 has been disclaimed.

[21] Appl. No.: 912,254

[22] Filed: Jul. 13, 1992

Related U.S. Application Data

[63] Continuation-in-part of Ser. No. 722,917, Jun. 28, 1991, Pat. No. 5,181,393, which is a continuation-in-part of Ser. No. 490,302, Mar. 8, 1990, abandoned.

[51] Int. Cl.⁵ .............................................. F25D 23/00
[52] U.S. Cl. ..................... 62/264; 62/176.1; 62/457.1; 220/87.1; 362/94; 422/24; 422/292
[58] Field of Search ............... 62/264, 457.1, 371, 62/334, 176.1; 362/94; 422/5, 24, 292; 248/147; 220/87.1

[56] References Cited

U.S. PATENT DOCUMENTS

| | | | |
|---|---|---|---|
| 1,789,268 | 1/1931 | Anderson | 62/176.1 |
| 2,010,799 | 8/1935 | Sexton | 362/94 |
| 3,041,852 | 7/1962 | Palmer | 62/334 |
| 3,161,030 | 12/1964 | Brewton | 62/457.9 |
| 4,902,482 | 2/1990 | Faust | 422/24 |

OTHER PUBLICATIONS

Microbiology Principles and Applications By: Joan G. Creager, Jacquelyn G. Black and Vee E. Davidson.

Primary Examiner—Ronald C. Capossela
Attorney, Agent, or Firm—Hopkins & Thomas

[57] ABSTRACT

A refrigerated waste storage container is disclosed, the container having a refrigeration unit for cooling or freezing the contents therein and a germicidal lamp for producing radiation to kill microorganisms in the waste. The container includes a sealable cover which incorporates the germicidal lamp and appropriate controls for cycling the lamp and the refrigeration unit to eliminate objectionable odors and germs.

19 Claims, 3 Drawing Sheets

REFRIGERATED WASTE CONTAINER WITH GERMICIDAL LAMP

RELATED APPLICATION

This application is a continuation-in-part of co-pending application Ser. No. 07/722,917, filed Jun. 28, 1991, now U.S. Pat. No. 5,181,393, entitled "Refrigerated Waste Container With Germicidal Lamp," by Gene Lott, also the inventor herein, which is a continuation-in-part of application Ser. No. 07/490,302, filed Mar. 8, 1990, now abandoned.

BACKGROUND OF THE INVENTION

Virtually every facility, whether commercial or residential requires that waste storage capability be provided. The present invention is directed to a storage means for homes, medical facilities, restaurants, and other places in which the waste is subject to decay, odor, and is potentially a source of infection. In U.S. Pat. No. 3,041,852 to Palmer, a refrigerated garbage storage container assembly is disclosed, with cooling provided by an external refrigeration system. A similar device is disclosed in U.S. Pat. No. 3,161,030 to Brewton, for a garbage container with a self-contained refrigeration unit. In both of these references, refrigeration is supplied to chill household garbage to reduce odor, decay, and consequently to lessen or eliminate insect problems while the garbage is being stored indoors prior to is ultimate disposal. U.S. Pat. No. 4,902,482 to Faust shows a receptacle for receiving waste in which an ultraviolet light irradiates the waste whenever the lid is closed for killing bacteria therein. The device also has a venting arrangement for maintaining the upper part of the receptacle at a lower pressure than the atmosphere outside the container.

Without cooling or other treatment, household garbage can produce many undesirable effects, such as odor problems and bacterial contamination as decay occurs. Medical wastes can harbor numerous pathogenic organisms. In restaurants, bacteria from decaying food on table linens can cause deterioration of the fabric while the linens are stored prior to cleaning. Households with infants or young children experience odor and other problems from diaper pails used for retaining cloth diapers prior to cleaning or from garbage containers used to temporarily hold soiled disposable diapers.

Corollaries to the storage problems are the large amounts of waste produced and the problem of ultimate disposal, typically in landfills. A good example of these problems is the controversy regarding the use of disposable diapers versus cloth diapers. Disposable diapers are very convenient, however, the plastic materials used in the diaper shell and some other components of the absorbent liners are not biodegradable. The popularity of the diapers leads to their widespread use and eventual disposal in a landfill. Landfill space is rapidly filling up resulting in some large municipalities having to ship garbage by train or truck to adjoining or even distant states. While the use of cloth diapers would alleviate this problem somewhat, such an alternative is less attractive to the consumer when compared to the throw-away convenience of disposable diapers, as the cloth diapers must be rinsed and washed or stored pending their pick-up by a diaper service.

SUMMARY OF THE INVENTION

It is, therefore, one of the principal objects of the present invention to provide a refrigerated waste container of self-contained design for receiving household, industrial and medical wastes, used cloth or disposable diapers, and other waste articles, the container having a refrigeration system operable within a range of from slight cooling to below freezing.

Another object of the present invention is to provide a refrigerated waste container which includes means for disinfecting waste material by inhibiting or killing bacteria, viruses, and other pathogenic organisms using germicidal lamps, fluids, or the like.

A further object of the present invention is to provide a refrigerated waste container that is easy to use, empty, and clean when necessary, which is relatively lightweight for easy portability, and which is durable for providing a long service life.

These and other objects are attained by the present invention which relates to a refrigerated waste container means having a means for inhibiting or killing microorganisms, such as a germicidal lamp, incorporated therewith. The container may be used for any waste material including children's diapers, cloth, or disposable, contaminated medical wastes, table linens, etc. A refrigeration unit, operable within a range of slight cooling to below freezing, is utilized for reducing the temperature within the container to a selected level partially dependent on the type of waste material to be placed therein. The present container is normally self-contained and portable, using a conventional power source such as electricity, propane, or the like. Control means are included for cycling the refrigeration unit and the germicidal lamp or the like when the container is closed and/or sealed.

Various additional objects and advantages of the present invention will become apparent from the following detailed description, with reference to the accompanying drawings.

DETAILED DESCRIPTION OF THE PREFERRED EMBODIMENT

Figure 1:
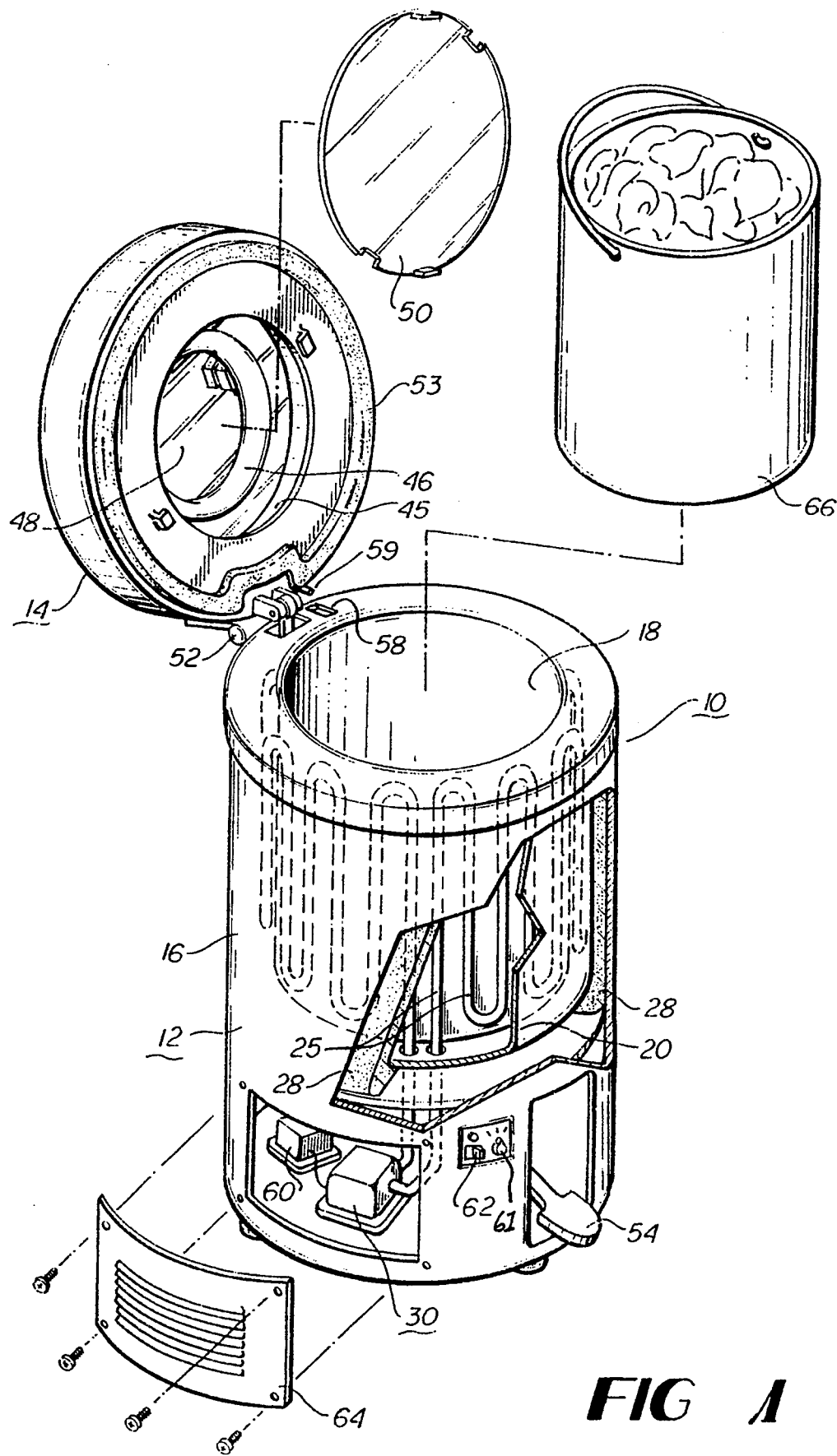
FIG. 1 is an exploded perspective view, shown partially in cross-section, of an embodiment of the refrigerated waste container.

Referring now more specifically to the drawings, and to FIG. 1 in particular, numeral 10 designates generally the present refrigerated waste container, shown in exploded form. The container includes a housing 12 with a lid or cover means 14 operatively associated therewith. The housing and lid may be formed from any number of suitable materials such as plastic, stainless steel, or others, or from a combination of materials. The housing and cover are essentially shells which contain the operative means of the present invention. In this regard, it will be noted from FIGS. 1 and 2 that the housing 12 includes an outer wall 16, an inner wall 18, and an intermediate wall 20 therebetween, the walls normally being spaced from one another and defining separate chambers. The inner wall 18 defines a chamber to be cooled, the chamber having a bottom or floor 22. A suitable drain (not shown) may be included for this inner chamber for washing and/or sanitizing purposes. The outer wall 16 also has a bottom or floor 24, this defining an insulation chamber. The intermediate wall defines a chamber for cooling means, such as refrigerator coils 25, this chamber having a bottom or floor 26. The outer chamber contains a suitable insulation material 28, which extends completely around the intermediate wall 20 and floor portion 26. The refrigerator coils, which may be externally disposed as well, are connected to a conventional, thermostatically controlled, refrigeration unit 30 which is powered by electricity, propane, solar energy or other suitable power source. A temperature gauge (not shown) may also be provided to indicate and sense the temperature inside the container.

The cover 14 of the present container is also formed as a shell, having outer wall 40, an inner wall 42, and a suitable insulation material 44 disposed therebetween. The cover has a recess 45 formed therein which houses a germicidal, normally ultraviolet (UV) lamp 46. Mounted in the recess above the lamp, if viewing the cover in a closed position, is a reflector means 48. Below the lamp, again with the cover in a closed orientation, is a UV-transparent, protective access cover 50. The germicidal lamp is typically a low-pressure mercury lamp which generates ultraviolet (UV) radiation in the 200–300 nanometer range. Other suitable lamps are available, for example, lamps which produce UV radiation and ozone, the ozone being a bactericidal and fungicidal agent as well. A further benefit from an ozone producing lamp is that the ozone is carried by air currents to places in the container that may not be reached by the UV radiation.

The effectiveness of UV radiation is known and proven, given adequate intensity and duration of exposure, however, the necessary exposure time varies considerably with the type and size of the microorganism and the medium within which the microorganisms are present. In general, the higher the temperature, the lower the UV requirements necessary to kill or inactivate microorganisms. However, the present invention overcomes this potential disadvantage since the lamps are more effective in low humidity environments, as is present in the inner, cooled chamber of the container 12. Thus, the present invention provides a previously unexpected and novel synergistic effect. The UV radiation is effective against airborne and surface bacteria, fungus, including yeast and mold spores, and viruses. The cold environment and the cycled UV radiation disrupt the life and reproductive cycles of the microorganisms, thus reducing decay and odor, and making the contaminated material much safer to handle for workers, parents, etc.

Figure 2:
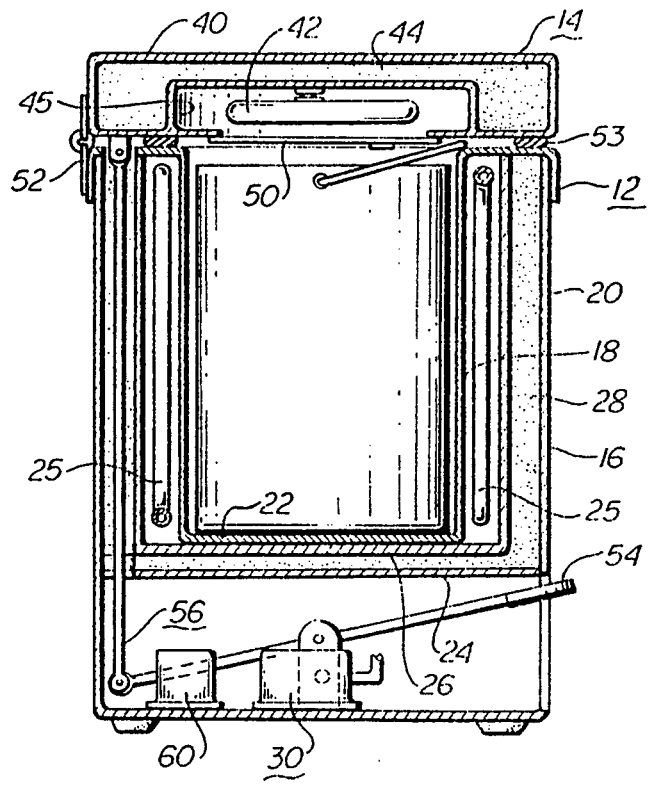
FIG. 2 is a side elevational and partial cross-sectional view of the present container.

The cover 14 is hingedly attached to the housing 12 with hinge means 52, and includes a suitable seal means 53 near the outer perimeter thereof where the cover meets the top of the container. A foot pedal 54 is provided for raising and lowering the cover, utilizing appropriate linkage; however, the mechanism may also include damping means, such as pneumatic cylinders, for assisting in raising and lowering the cover, or other appropriate means. Similarly, the cover may also be of the completely detachable type, rather than being hingedly connected. When the foot pedal is depressed to open the container, a switch means 58 is moved, the switch means serving to control the lamp 46. The switch means is preferably of the pin-type, with pin 59 pressing the switch on when the cover is fully closed. The pin loses contact with the switch as soon as the cover is opened to turn-off the lamp. The system is designed to shut off the light as soon as the cover is opened to avoid any exposure of the user to the UV light since the UV radiation can cause conjunctivitis (inflammation of the outer membrane of the eyes) and a reddening, or even burns, of the skin, similar to sunburn. The system also includes a suitable timer 60, which serves to cycle the germicidal lamp with a manual adjustment control means 61, and other appropriate controls which normally includes an on-off switch 62. As shown in FIGS. 1 and 2, the timer, refrigeration unit, and parts of the linkage for the foot pedal may be conveniently housed in the lower portion of the housing 12, with access being provided through door 64. In normal operation, the thermostat activates the refrigeration cycle shortly after the lamp lights, due to the heat produced thereby, and then deactivates the cycle when the desired temperature is reached. Appropriate control circuitry is provided, such circuitry being known in the art.

As noted hereinabove, the refrigeration system is thermostatically controlled in a conventional manner. Thus, where heat is introduced into the container from the UV source or from opening the container, the thermostat will cause the compressor to operate, lowering the temperature. The lamp is wired to shut off when the lid is raised and also includes an adjustable cycling means or timer. This permits the user to adjust the duration and timing of the lamp cycle depending on the material placed therein. For example, since prolonged exposure to UV radiation weakens fabrics and causes colors to fade, when the present device is used for linen or fabric storage the timer would be set for short duration exposures at relatively prolonged intervals. When the present device is used for cloth diaper storage, slightly longer intervals would be set due to the increased moisture content while still minimizing fabric weakening. When disposable diapers are being stored, even longer intervals of exposure are used thereby providing an additional environmental benefit in that UV radiation helps to degrade the plastic covering of such diapers. Such adjustments may be made automatically using a moisture sensor (not shown), similar to sensors used in clothes dryers, with the manual override on-off switch 62 normally provided for adjustments based solely on contents.

The present container also includes an auxiliary container means such as pail 66 which nests inside the inner, cooled chamber and is removable therefrom. The pail may be conveniently utilized to hold diapers, for example, until they are picked up by a diaper service, in the case of cloth diapers, or discarded, in the case of disposable diapers.

Figure 3:
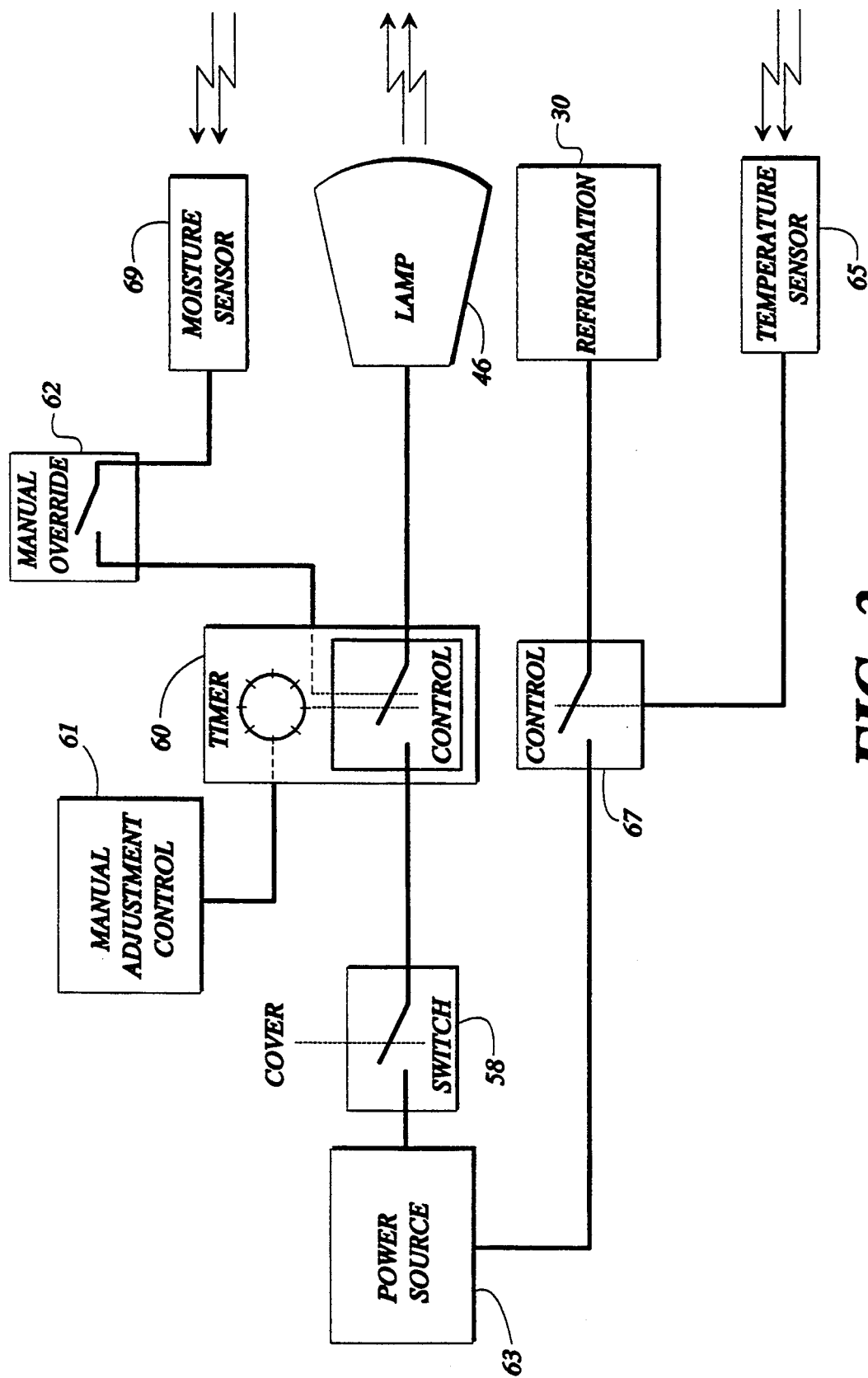
FIG. 3 shows an example of control circuitry for the present container.

FIG. 3 shows an example of control circuitry for the present invention. As shown in FIG. 3, the refrigeration unit 30 is powered by a power source 63. A temperature sensor 65, or thermostat, is disposed to sense the temperature inside the container 10 and control the refrigeration unit 30, as indicated by control 67. As further shown in FIG. 3, the switch means 58 serves to control power to the lamp 46. The switch means 58 is actuated by the cover 14. In the preferred embodiment, the switch means 58 turns on the lamp 46 when the cover 14 is closed and turns off the lamp 46 when the cover is opened. The timer 60 is also shown in FIG. 3. The timer 60 serves to cycle the germicidal lamp 46. The manual adjustment control 61 permits the user to adjust the duration and timing of the lamp cycle depending on the material placed within the container 10. Finally, the manual sensors 69, disposed to sense moisture in the container 10, can be connected by manual on-off switch 62 as indicated in FIG. 3 to control illumination of the lamp 46.

Figure 4:
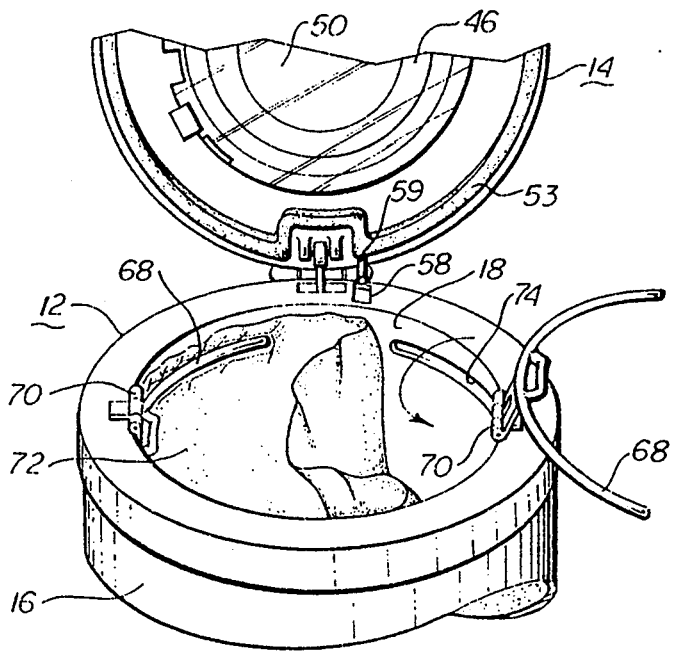
FIG. 4 is a partial perspective view illustrating an alternate embodiment of the invention.
Figure 5:
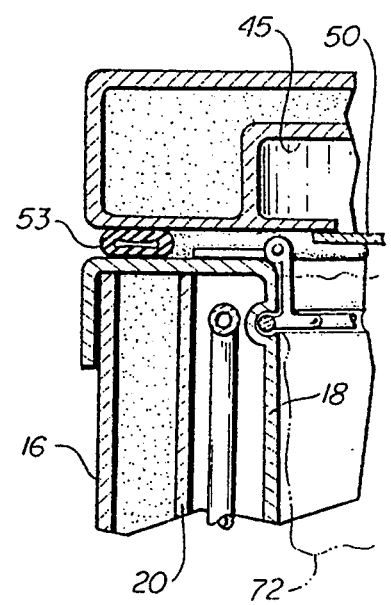
FIG. 5 is a partial, cross-sectional view illustrating the alternate embodiment with the lid closed.

Referring to FIGS. 4 and 5, an alternate embodiment of the present invention is shown, illustrating a means for securing a trash bag or the like. While shown separately for the sake of clarity, the securing means present no obstacle to the use of the pail 66. The securing means include one or more pivotally mounted bar means which pivot outwardly on hinges 70 to allow placement or removal of a bag 72. When the bag is inserted, as shown in FIG. 4, the bar means are pivoted to a closed position, disposed inside the container, and are received in corresponding slot means 74. This arrangement permits the use and securement of a paper, plastic or cloth bag, for example, for holding disposable diapers or other items in a cold storage condition until their ultimate disposal and/or recycling.

As noted previously, the present waste container is capable of reducing temperatures therein within a range of from slight cooling below ambient temperatures to below freezing levels, i.e. less than 0° C. This provides a synergistic, destructive effect on microorganisms through the combination of cold temperatures, low humidity, and ultraviolet radiation from the germicidal lamp 46.

The present invention, by cooling or freezing waste materials such as household garbage, soiled diapers, medical waste and the like, in combination with the germicidal lamp, eliminates most, if not all offensive odors produced by decay engendered by microorganisms. In addition, the waste is made safer and easier to handle by virtue of the germicidal and refrigerating processes. The present invention can also contribute to the lessening of the continuing trash disposal crisis through encouraging the use of recyclable materials, such as cloth diapers, by making storage of the materials between pick-ups, washings, etc., much less objectionable.

The invention has been illustrated as cylindrical; however, this is not meant to be limiting in any sense. It is contemplated that the concepts described herein can be employed in containers of any size, from wastebaskets to large trash dumpsters. Similarly, the power source may be electricity, batteries, dry ice, propane and even solar energy for large outdoor applications such as dumpsters. It is contemplated also that the present invention can be used in aircraft, trains, buses and the like.

Refrigeration may also be accomplished through the use of electromagnetic or fluid means. Similarly, fluid may be employed as a germicidal agent, the fluid only being dispensed when the cover means is closed and/or sealed.

Thus, while an embodiment of a refrigerated waste container with germicidal lamp means and modifications thereof have been shown and described in detail herein, various additional changes and modifications may be made without departing from the scope of the present invention.

I claim:

1. A waste storage device for retarding bacterial growth by irradiating waste material in a low humidity, cool environment comprising:
   a container means having a cover means with a seal means disposed between said container means and said cover means, said cover means including a recess formed therein,
   refrigeration means operatively associated with said container means for refrigerating said container means and the contents thereof and lowering the humidity in said container means, and
   radiation producing means disposed within said recess in said cover means for irradiating the contents therein when said cover means is in a closed position.

2. A waste storage device as defined in claim 1 in which said radiation producing means includes a germicidal lamp producing ultraviolet radiation and also includes switch means operatively associated with said cover means for activating said lamp when said cover means is in a closed position, said cover means further including a protective cover for said lamp disposed in closing relationship with said recess.

3. A waste storage device as defined in claim 1 in which said cover means includes a foot pedal with linkage associated therewith and with said cover means for raising and lowering said cover means, and said cover means also includes insulation means disposed around said recess.

4. A waste storage device as defined in claim 1 in which said device includes a manual control means for cycling said refrigeration means and said radiation producing means.

5. A waste storage device as defined in claim 4 in which said radiation producing means includes a germicidal lamp producing ultraviolet radiation for killing microorganisms in the waste material.

6. A waste storage device as defined in claim 1 in which said device further includes a thermostat means for sensing the temperature in said container means and for controlling said refrigeration means.

7. A waste storage device as defined in claim 1 in which said device also includes moisture sensing means for automatically cycling said radiation producing means in response to the relative humidity in said container means.

8. A waste storage device for retarding bacterial growth by irradiating waste material in a low humidity, cool environment comprising:
   a container means for holding the waste material, said container means having a cover means for sealing said container means,
   seal means disposed between said container means and said cover means, said cover means including a recess formed therein,
   refrigeration means for refrigerating the waster material and for lowering the humidity in said container means,
   radiation producing means disposed within said recess in said cover means for irradiating the waste material in said container means, said radiation producing means being operable when said cover means is disposed in sealing relationship with said container means and being inoperable when said cover means is removed therefrom for introducing and removing waste material from said container means.

9. A waste storage device as defined in claim 8 in which said radiation producing means includes a germicidal lamp producing ultraviolet radiation and also includes switch means operatively associated with said cover means for activating said lamp when said cover means is in a closed position.

10. A waste storage device as defined in claim 8 in which said cover means includes a foot pedal with linkage associated therewith and with said cover means for raising and lowering said cover means and said cover means also includes a reflective means disposed so as to reflect radiation into said container means.

11. A waste storage device as defined in claim 8 in which said device includes manual control means for cycling said refrigeration means and said radiation producing means.

12. A waste storage device as defined in claim 11 in which said radiation producing means includes a germicidal lamp producing ultraviolet radiation for killing microorganisms in the waste material.

13. A waste storage device as defined in claim 8 in which said device further includes moisture sensing means for automatically cycling said radiation producing means in response to the relative humidity in said container means.

14. A waste storage device as defined in claim 8 in which said device further includes a thermostat means for sensing the temperature in said container means and for controlling said refrigeration means.

15. A waste storage device for retarding bacterial growth by irradiating waste material in a low humidity, cool environment comprising:

a container means for holding the waste material, said container means having a cover means for sealing said container means, refrigeration means for refrigerating the waste material and for lowering the humidity in said container means, radiation producing means disposed within the cover means for irradiating the waste material in said container means, said radiation producing means being operable when said cover means is disposed in sealing relationship with said container means and being inoperative when said cover means is removed therefrom for introducing and removing waste material from said container means, and manual control means for adjustable cycling said radiation producing means depending upon the waste material placed in said container means.

16. A waste storage device as defined in claim 15 in which said radiation producing means includes a germicidal lamp producing ultraviolet radiation and also includes switch means operatively associate with said cover means for activating said lamp when said cove means is in a closed position.

17. A waste storage device as defined in claim 15 in which said device also includes moisture sensing means for automatically cycling said radiation producing means in response to the relative humidity in said container means.

18. A waste storage device as defined in claim 15 in which said device further includes a thermostat means for sensing the temperature in said container means and for controlling said refrigeration means.

19. A waste storage device as defined in claim 15 in which said cover means includes a foot pedal with linkage associated therewith and with said cover means for raising and lowering said cover means, and said cover means also includes a reflective means disposed so as to reflect radiation into said container means.

* * * * *